United States Patent [19]

Meijer

[11] Patent Number: 5,089,228

[45] Date of Patent: Feb. 18, 1992

[54] METHOD FOR STERILIZING AND DISPOSING OF INFECTIOUS WASTE

[75] Inventor: Robert S. Meijer, San Diego, Calif.

[73] Assignee: Winfield Corporation, San Diego, Calif.

[21] Appl. No.: 511,275

[22] Filed: Apr. 19, 1990

[51] Int. Cl.[5] .............................................. A61L 2/16
[52] U.S. Cl. .......................................... 422/37; 241/17; 241/22; 241/DIG. 38; 422/26; 422/27; 422/29; 422/32; 422/38; 422/295; 422/307; 422/309; 423/DIG. 18; 423/DIG. 20
[58] Field of Search ........................ 422/26, 27, 29, 37, 422/38, 32, 295, 307, 309; 423/DIG. 18, DIG. 20; 241/17, 22, DIG. 38

[56] References Cited

U.S. PATENT DOCUMENTS 4,822,513  4/1989  Corby ..................................... 422/32
4,923,677  5/1990  Simon et al. ........................... 422/28

OTHER PUBLICATIONS

Medical Safe TEC, Inc., Series Twelve Five, "The Ultimate in Total Destruction and Decontamination of Infectious Waste and Tot. Inf. Waste Disp. Spec." Smashing Success, newspaper article.

*Primary Examiner*—Timothy M. McMahon
*Attorney, Agent, or Firm*—Nydegger & Associates

[57] ABSTRACT

A method for sterilizing infectious waste includes placing the waste in a disposal apparatus which has an isolated volume for holding the waste. A dry granulated medium which has a disinfectant constituent is also placed within the isolated volume along with the waste. When the disposal apparatus is activated, an atomized mist is introduced into the volume and the waste, the medium, and the moisture in the mist are thoroughly blended together. The resulting destroyed waste is thoroughly moistened with the disinfectant solution which is formed by the mist and the disinfectant constituents of the medium. Then, the moistened, destroyed waste is heated to a predetermined temperature for a predetermined time to ensure efficacious sterilization of the waste.

6 Claims, 1 Drawing Sheet

METHOD FOR STERILIZING AND DISPOSING OF INFECTIOUS WASTE

FIELD OF THE INVENTION

The present invention relates generally to methods for disposing of infectious waste. More particularly, the present invention relates to methods which mechanically destroy and sterilize infectious waste. The present invention is particularly, though not exclusively, useful for mechanically destroying infectious waste in an industrial blender and simultaneously sterilizing the waste with a disinfectant that can be stored in a dry form.

BACKGROUND OF THE INVENTION

The disposal of infectious waste from hospitals and other medical establishments is a major problem. Indeed, the importance of proper and effective infectious waste disposal has become of greater concern in recent years, due to an increased awareness of health problems such as the AIDS epidemic. In part because of the AIDS epidemic, definitions of what constitutes "infectious waste" are being broadened. Consequently, the volume of infectious waste which must be disposed of is increasing. Accordingly, the need for a system or apparatus which will accomplish the safe, efficacious, and cost effective disposal of significant volumes of infectious waste is growing.

One method for sterilizing and disposing of infectious waste involves incineration, wherein the waste is burned and the decontaminated ashes are properly disposed of. An alternative waste disposal method is to sterilize the waste in a steam autoclave or ethylene oxide autoclave prior to waste disposal. While effective for their intended purposes, both incinerators and autoclaves present ancillary waste disposal problems. Incinerators, for example, are difficult and costly to construct and are relatively expensive to maintain in an environmentally safe manner. Autoclaves too, present additional problems, such as the need to monitor the processed waste for 100% microbial kill. Additionally, waste which has been sterilized by autoclaving typically requires further disposal procedures, such as incineration, prior to final disposition of the waste in such places as ordinary landfills.

With the above discussion in mind, alternative infectious waste disposal systems have been proposed to disinfect waste which has already been mechanically shredded into small particles. According to these proposals, after the shredding process, a mist of a disinfectant solution containing a chlorine compound is sprayed onto the shredded waste in order to sterilize the waste. The decontaminated liquid constituents of the resulting slurry effluent may then be separated from the solid constituents of the effluent and disposed of in an ordinary waste disposal system. Then, the decontaminated solid constituents of the effluent may be disposed of in ordinary landfills.

Unfortunately, decontamination of waste using liquified chlorine presents certain technical complications. First, liquified disinfectant loses its disinfectant potency during prolonged storage. Thus, there is a need to use liquified disinfectant that is relatively "fresh" in order to achieve an acceptable degree of waste decontamination. Second, it is relatively difficult to ensure that an appropriate amount of the disinfectant has been sprayed onto the waste during the disposal process. This is because an appropriate amount of disinfectant must contact the waste in order for the decontamination process to be efficacious. It is also important, however, to avoid spraying too much chlorine into the disposal chamber of the sterilization apparatus, in order to avoid certain undesirable results, such as the release of toxic gasses. The present invention recognizes that precise amounts of a dry chlorine compound which can be stored for a relatively lengthy period without losing its potency can be mixed with water and used to sterilize infectious waste in systems that mechanically destroy the waste.

Accordingly, it is an object of the present invention to provide a method for waste disposal in which precise amounts of a dry chlorine-containing medium are mixed with water and blended with infectious waste to sterilize the waste. Another object of the present invention is to provide a method for waste disposal which results in the destruction of infectious waste while the waste is being sterilized. Finally, it is an object of the present invention to provide a method for waste disposal which is relatively easy and comparatively cost-effective to implement.

SUMMARY

The method for sterilizing infectious waste in accordance with the present invention includes placing the waste into an appropriate disposal apparatus, such as an industrial blender, which has an isolated volume for holding and mechanically destroying the waste. A dry granulated medium which contains a disinfectant constituent, such as sodium hypochlorite, is also placed within the isolated volume along with the infectious waste. The granulated medium may also include pH-adjusting constituents, deodorant constituents, and surfactants, in addition to a pigment constituents for staining the waste during the destruction process. After the waste has been ingested into the disposal apparatus, the disposal apparatus is activated to destroy the waste, such as by blending and chopping the waste. During the destruction process, water in the form of an atomized mist is introduced into the isolated volume. The water forms a decontamination solution with the disinfectant constituent as the solution moistens the waste during the destruction process. Consequently, the destruction process results not only in the mechanical destruction of the waste but also in the thorough moistening of the destroyed waste with the decontamination solution.

To ensure efficacious sterilization is achieved, the moistened, destroyed waste is heated to a predetermined temperature greater than approximately 160° F. for a predetermined time period of at least thirty seconds duration. Thus, the destroyed and stained waste may eventually be identified as sterilized waste subsequent to the sterilization process.

In the preferred embodiment of the present invention, the infectious waste is initially placed into an infectious waste bag which has a container for holding the waste and has an enclosed pouch attached to the container. A predetermined amount of the dry granulated medium containing the disinfectant constituent is held within the pouch. After the infectious waste has been discarded and placed in the bag, the bag and its contents are placed in the disposal apparatus. During the destruction process described above, the pouch is ruptured to release the medium onto the waste. When this medium contacts the atomized mist, the mist and the disinfectant constituent of the medium form a decontaminating solution which is thoroughly mixed with the waste to sterilize the waste as the waste is being mechanically destroyed.

To remove the destroyed waste from the disposal apparatus, an auger may be connected to the outlet of the blender. As the destroyed waste enters the auger from the blender, it is further mixed, compressed, and transported by the auger as the auger is rotated to convey the waste to the outlet of the isolated volume of the apparatus. The speed of rotation of the auger is established to ensure the waste is held within the heated, isolated volume of the apparatus for the duration of the predetermined sterilizing time period.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
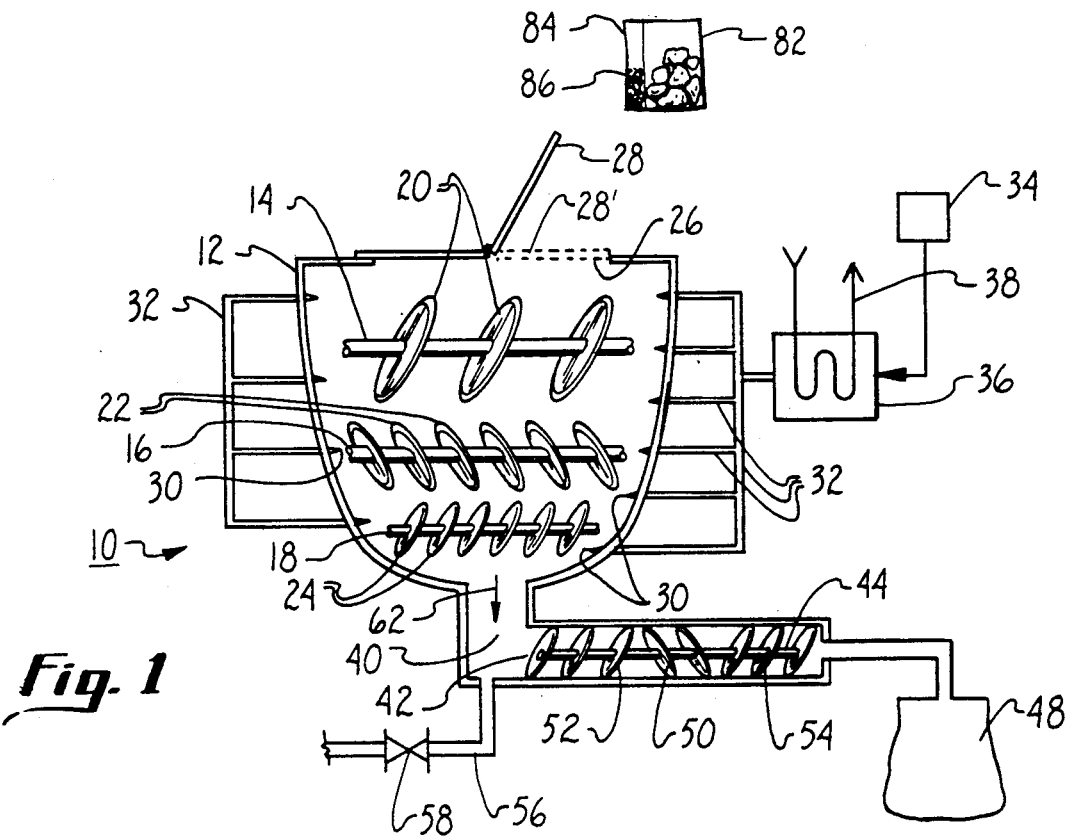
FIG. 1 is a schematic diagram of one type of apparatus which may be used in conjunction with the novel method of the present invention.

Referring initially to FIG. 1, one type of waste disposal apparatus, generally designated 10, is shown which may be used in conjunction with the present invention. It is to be understood, however, that while the apparatus 10 is schematically shown in FIG. 1 as being a particular type of blender, any apparatus which can perform the below-disclosed steps of the present invention may be used, such as, for example, industrial choppers, shredders, hammermills, or other types of blenders. Importantly, apparatus 10 must be capable of mechanically destroying, such as by chopping, pulverizing, or the like, items which are typically discarded as infectious waste, such as for example, syringes, glass, plastic, cloth, etc.

As seen in FIG. 1, apparatus 10 comprises a blender 12 which has three rows 14, 16, 18 of successively smaller shredding discs 20, 22, 24. The discs 20, 22, 24 blend, or pulverize, glass, plastic, cloth, etc. which passes through blender 12. As shown in FIG. 1, discs 22 of row 16 may be oriented in a counter rotating relationship with respect to discs 20, 24 of rows 14, 18. Alternatively, the individual discs of each of the rows 14, 16, 18 may be oriented on their respective rows in counter rotating relationships with the other discs of that row. In either case, waste may be deposited in blender 12 through inlet 26 when plate 28 is in its open position. When plate 28 is in its closed position 28, shown in phantom in FIG. 1, plate 28 establishes an air tight seal over inlet 26.

Still referring to FIG. 1, a plurality of atomizing mist nozzles 30 are shown positioned inside blender 12. These nozzles 30 are connected to fluid lines 32, which are in turn connected to a fluid source 34 through heat exchanger 36. Fluid from source 34 may be pumped through lines 32 by a suitable pump (not shown). The fluid in lines 32 is conductively cooled or heated, as appropriate, by physical contact with line 38, through which flows a heat exchange medium (not shown). The fluid from source 34 may be pure water or may be water which includes certain chemical constituents. For example, these chemical constituents may include disinfectant constituents, deodorant constituents, acidity-adjusting constituents, surfactants, and pigment constituents.

At the outlet 40 of blender 12, an outlet passage 42 is formed in which is disposed an auger 44. By a well known mechanical process, auger 44 draws waste through passage 42 and discharges the waste to a bag 48. As shown in FIG. 1, auger 44 may comprise a series of left-hand flutes, such as flute 50, and right-hand flutes, such as flutes 52, 54. Thus, in the exemplary embodiment shown in FIG. 1, auger 44 is a compounding screw auger. Importantly, auger 44 is disposed in passage 42 such that auger 44 forms an aerosol block at outlet 40. Accordingly, waste can pass through passage 42 only when auger 44 is rotated. Finally, to drain liquid from blender 12, a drain line 56 is connected to outlet 40. To isolate line 56, a valve 58 is attached in fluid communication with line 56.

Importantly, the interior volume of apparatus 10 which is defined by blender 12 and passage 42 is an isolated volume. Stated differently, when auger 44 is stationary and plate 28 and drain valve 58 are closed, no potentially infectious air or fluid may escape from apparatus 10. Thus, the destruction and sterilization of infectious waste by apparatus 10 occurs in a volume which is isolated from the surrounding environment.

METHOD OF STERILIZATION

Figure 2:
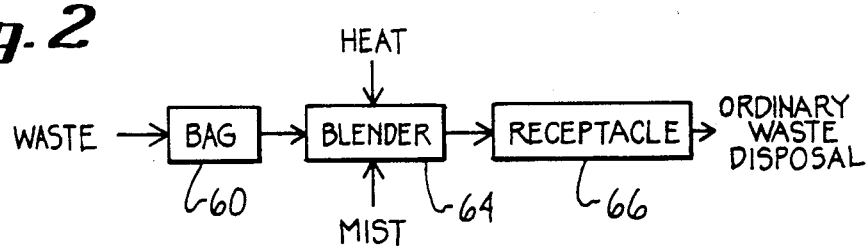
FIG. 2 is a block diagram of the novel method of the present invention.

In cross-reference to FIGS. 1 and 2, the method of the present invention for sterilizing waste may be seen. First, infectious waste which is to be sterilized in apparatus 10 may be placed in a suitable bag 82, as indicated at block 60 of FIG. 2. Infectious waste bag 82 may also contain a pouch 84 that holds a predetermined amount of a medium 86 which has suitable disinfectant constituents, preferably granulated sodium hypochlorite. Additionally, the medium may contain a surfactant constituent to prevent beading of solutions which may subsequently be formed when moisture contacts the medium. Lastly, the medium may contain pH-adjusting constituents, deodorant constituents, and pigment constituents. Plate 28 is then moved to its open position and the bag 82 which contains the infectious waste and disinfectant constituents is placed inside blender 12. Alternatively, infectious waste may be placed directly into blender 12 without first placing the waste in bag 82 at step 60. In such an instance, the predetermined amount of the medium which contains the sodium hypochlorite is also placed directly into blender 12 along with the infectious waste. In either case, once the infectious waste and the granulated medium have been placed inside blender 12, plate 28 is moved to its closed position to seal inlet 26 of blender 12.

Once inlet 26 is sealed, blender 12 may be activated, as indicated by block 64 in FIG. 2, to destroy the infectious waste bag 82 and the infectious waste held therein. More specifically, as the successively smaller discs 20, 22, 24 rotate, the bag 82 and its pouch 84 are ruptured to release the medium 86 onto the waste. Then, the infectious waste is pulverized, or blended, into successively finer pieces and is thoroughly mixed with the disinfectant-containing medium 86 as the waste passes down through blender 12 in the direction of arrow 62. This mixing is made even more thorough by using discs 20, 22, 24 that are disposed in counter rotating rows 14, 16, 18, as described above.

Additionally, as the infectious waste is pulverized, it is moistened with an atomized mist that is directed into blender 12 through nozzles 30. This mist is a liquid, preferably water from source 34 which is atomized by nozzles 30 as it passes through nozzles 30. For purposes of the present invention, sufficient mist is injected into blender 12 to thoroughly moisten the waste inside blender 12. It is also desireable, however, to limit the volume of mist that is injected into blender 12 in order to avoid forming an excessive amount of liquid inside blender 12. In the event that excess liquid is formed, such excess liquid may be drained through line 56 by opening valve 58 after the waste sterilization process.

The liquid from source 34 may also contain certain chemicals and reagents, if desired. For example, the liquid in source 34 may contain a pigment for staining the waste during the sterilization process to subsequently identify the waste as sterilized waste. Further, the liquid from source 34 may contain acidity adjusting chemicals to adjust the pH of the disinfectant solution that is formed when the mist mixes with the disinfectant constituents in blender 12. Additionally, the liquid from source 34 may contain a deodorant and a surfactant to prevent beading of the disinfectant solution. Alternatively, the dry disinfectant-containing medium which is placed in blender 12 along with the infectious waste may also contain one or more of the pH adjusting chemicals, surfactants, deodorants, or pigment constituents discussed above. In any event, the mist forms a disinfectant solution with the disinfectant constituent of the granulated medium inside blender 12. This disinfectant solution is thoroughly mixed with the infectious waste as the waste is pulverized.

Block 64 of FIG. 2 indicates that as the infectious waste is pulverized and moistened with the disinfectant solution, it is also heated. Heating the waste is desireable because, as is well known in the art, sterilization of infectious waste by exposing the waste to certain disinfectants, such as chlorine dioxide, is more efficaciously accomplished at relatively higher temperatures. Heating of the waste may be effected in several ways, such as by installing heating elements within blender 12. In the preferred embodiment, however, the liquid from source 34 is heated before the liquid is injected in the form of an atomized mist into blender 12. Heating the liquid from source 34 may be done by a variety of methods, such as by passing the liquid through heat exchanger 36. A heating medium may then be directed to flow through line 38. Line 38 is preferably made of a thermally conductive material. The heat in the heating medium is conductively transferred to the liquid from source 34 as the liquid flows past and contacts line 38 inside heat exchanger 36.

As the skilled artisan will recognize, waste within blender 12 will also be mechanically heated as a result of the pulverizing, or blending process. Indeed, depending on a number of factors, the blending process itself may impart sufficient heat to the waste being blended so that the liquid from source 34 may not have to be heated prior to being injected into blender 12. In certain cases, the blending process may generate such large amounts of heat that the liquid from source 34 may even have to be cooled prior to injection into blender 12. In such a case, the temperature of the medium flowing through line 38 will be lowered accordingly.

After being pulverized, heated, and moistened with the disinfectant solution which is formed as disclosed above, the waste enters passage 42. The waste is drawn through passage 42 by the activation and consequent rotation of auger 44. Recall that waste cannot pass through passage 42 until auger 44 is rotated, because auger 44 otherwise establishes an aerosol block at outlet 40 of blender 12. As the waste is drawn through passage 42, the waste is further mixed with the disinfectant solution. This mixing is made more thorough when a compounding screw auger 44, as described above, is used to draw waste through passage 42, as shown in FIG. 1. Compounding screw auger 44 also compresses the pulverized waste as the waste is drawn through passage 42. Liquid which may be squeezed out of the waste during this process may be drained through line 56 by opening valve 58. Additionally, to maintain the temperature of the waste at an appropriate level, auger 44 may be heated by suitable means.

As indicated at block 66 in FIG. 2, after passing through passage 42, the now-sanitized waste may be directed into a receptacle such as bag 48 in FIG. 1. Then, the receptacle may be disposed of using ordinary waste disposal techniques, such as by placing the receptacle in an ordinary waste landfill.

As disclosed above, the infectious waste is maintained in a moistened condition at a predetermined elevated temperature for a predetermined time as it is processed through apparatus 10. This is because the chlorine dioxide solution which is mixed with the moistened waste inside blender 12 more efficaciously sterilizes the waste at elevated temperatures. Preferably, the waste is maintained at a temperature of at least 160° F. for at least 30 seconds. Accordingly, the temperature inside apparatus 10 and the duration of the passage of infectious waste through apparatus 10 are controlled to establish the above time and temperature conditions.

Figure 3:
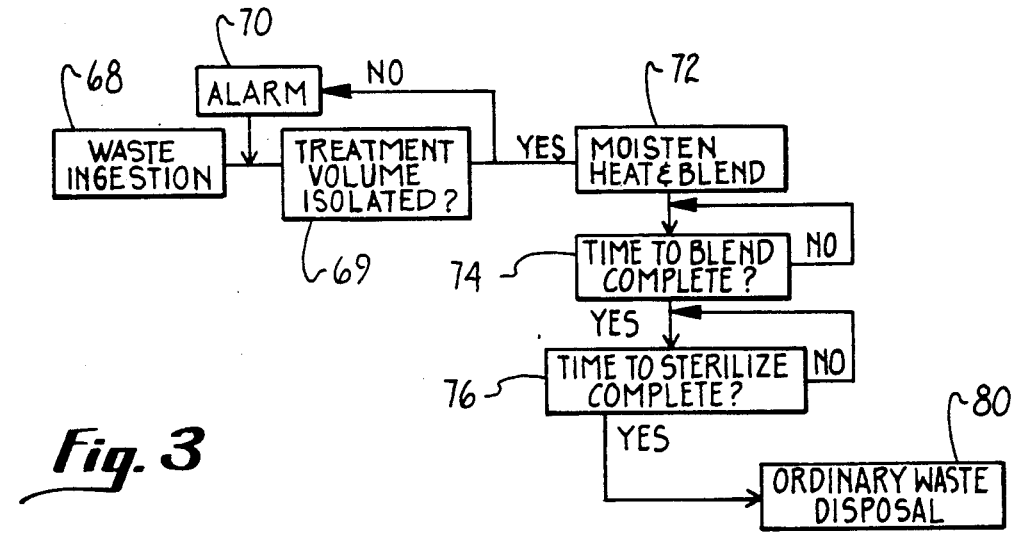
FIG. 3 is a block diagram which shows the logic of the novel method of the present invention.

FIG. 3 shows the logic used by the present invention to establish proper time and temperature conditions. First, waste is ingested into blender 12 as indicated at block 68. Next, the logic of the present invention determines whether the interior volume of blender 12 is isolated from the surroundings of apparatus 10, as indicated at block 69, before permitting activation of the blending discs 20, 22, 24. This is to ensure that potentially infectious aerosols which may be formed during the blending process do not escape the interior volume of blender 12. For the embodiment of apparatus 10 shown in FIG. 1, the interior volume of blender 12 is isolated when plate 28 and valve 58 are closed and auger 44 is deactivated (i.e. not rotating) If the interior volume of blender 12 is not isolated, an alarm may be activated at block 70. If the interior volume of blender 12 is isolated, the logic of the present invention permits activation of discs 20, 22, 24 of blender 12, indicated at block 72.

After activation of blender 12, the logic of the present invention counts down a predetermined time period to ensure that the infectious waste within blender 12 has been thoroughly blended and moistened with disinfectant solution. This step of the logic is represented by block 74 in FIG. 3. Once the time period for sufficient blending has elapsed, auger 44 is activated to draw the waste through passage 42. Next, to ensure adequate sterilization conditions are met, the logic of the present invention establishes an appropriate speed of rotation for auger 44. More specifically, the speed of rotation of auger 44 (and, hence, the speed with which waste is transported through passage 42) is established to ensure that the period during which waste is transported through passage 42 equals or exceeds the predetermined time period disclosed above. This step is indicated at block 76 in FIG. 3. After the waste has been transported through passage 42, the now-decontaminated waste is directed into receptacle 48 (shown in FIG. 1) as indicated at block 80 (shown in FIG. 3). The waste may then be disposed of as ordinary waste.

While the particular method for sterilizing and disposing of infectious waste as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A method for disinfecting an infectious waste in an isolated volume, which comprises the steps of:

placing said waste in a first compartment of a mechanically destructible bag;

placing a solid medium having disinfectant constituents into a second compartment of said bag;

sealing said second compartment to prevent communication between said first and second compartments;

placing said bag into said isolated volume;

mechanically destroying said bag to commingle said medium and said waste thereby forming a treatment mixture;

wetting said treatment mixture with an aqueous solvent heated to a predetermined temperature;

dissolving said medium in said solvent to form a treatment solution; and maintaining said waste in contact with said treatment solution for a predetermined time period.

2. A method for disinfecting an infectious waste in an isolated volume as recited in claim 1 wherein said predetermined temperature is greater than or equal to one hundred sixty degrees (160°) F. and said predetermined time period is greater than or equal to thirty (30) seconds.

3. A method for disinfecting an infectious waste in an isolated volume as recited in claim 1 wherein said medium further comprises a pigment constituent and said method further comprises the step of staining said waste with said pigment constituent during said destroying step.

4. A method for disinfecting an infectious waste in an isolated volume as recited in claim 1 wherein said disinfectant constituents comprise sodium hypochlorite.

5. A method for disinfecting an infectious waste in an isolated volume as recited in claim 1 wherein said bag is mechanically destroyed.

6. A method for disinfecting an infectious waste in an isolated volume as recited in claim 5 wherein said bag is destroyed by blending.

* * * * *